United States Patent [19]  [11] Patent Number: 4,804,768
Quirk et al. [45] Date of Patent: Feb. 14, 1989

[54] PROCESS FOR PRODUCING EPOXYORGANOALKOXYSILANES

[75] Inventors: Jennifer M. Quirk, Highland, Md.; Bernard Kanner, West Nyack, N.Y.

[73] Assignee: Union Carbide Corporation, Danbury, Conn.

[21] Appl. No.: 913,330

[22] Filed: Sep. 30, 1986

[51] Int. Cl.[4] .................... C07D 303/02; C07F 7/02
[52] U.S. Cl. .................................................... 549/215
[58] Field of Search .......................................... 549/215

[56] References Cited

U.S. PATENT DOCUMENTS

| | | | |
|---|---|---|---|
| 2,606,162 | 8/1952 | Coffey et al. | 269/22 |
| 2,970,150 | 1/1961 | Bailey | 549/215 |
| 3,950,364 | 4/1976 | Vahlensieck et al. | 549/215 |
| 4,028,384 | 6/1977 | Vahlensieck et al. | 549/215 |
| 4,083,856 | 4/1978 | Mendicino | 549/215 |

FOREIGN PATENT DOCUMENTS 580908 8/1959 Canada ................................ 549/215

OTHER PUBLICATIONS

Dickers et al, "Organosilicon Chemistry, etc.", 92:180380e (1980).
Bazant et al, "Organosilicon Chemistry, etc.", 84:165016g (1976).
Rejhon et al., "The Catalytic Activity of etc.", Collec. Czech. Chem. Comm., 40 3680 (1975).
"Latest Research on the Hydrosilylation Reaction", Russian Chemical Review, 46 (3), 1977, pp. 264-277.
"Organosilicon Compounds", Chemical Abstracts, vol. 84, 1986, p. 490, CA 84:165010a.

Primary Examiner—Richard L. Raymond
Assistant Examiner—Patricia L. Morris
Attorney, Agent, or Firm—Henry H. Gibson; Eugene C. Trautlein

[57] ABSTRACT

There is disclosed a process for producing certain epoxyorganoalkoxysilanes through the rhodium catalyzed hydrosilation of ethylenically unsaturated epoxides and alkoxysilanes in the presence of nitrogenous impurities.

17 Claims, No Drawings

PROCESS FOR PRODUCING EPOXYORGANOALKOXYSILANES

BACKGROUND OF THE INVENTION

1. Field of the Invention

The invention provides a process for producing epoxyorganoalkoxysilanes through a rhodium catalyzed hydrosilation of ethylenically unsaturated epoxides with alkoxysilanes in the presence of nitroqenous impurities.

2. Description of the Prior Art

The hydrosilation reaction was discovered in 1947 and over the years has become one of the best known and most widely practiced reactions in organosilicon chemistry. Hydrosilations are used in a wide variety of large scale commercial applications and have been the subject of several extensive reviews, i.e., *Organic Insertion Reactions of Group II Elements*, Consultants Bureau, N.Y., 1966; *Orqanometallic Compounds of the Group IV Elements*, Dekker, N.Y., 1968, Vol. I; *Preparation of Carbofunctional Orqanosilanes by an Addition Reaction*, Moscow, 1971; Russ Chem Rev., 46, 264 (1977); and J. Organometal Chem. Library 5, 1977, pp. 1-179.

Various transition metals are known to be effective as catalysts for the hydrosilation reaction. U.S. Pat. No. 2,823,218 teaches that chloroplatinic acid, a soluble form of platinum is a particularly effective hydrosilation catalyst. The reaction of unsaturated epoxides and alkoxysilanes provides a direct process for producing various epoxyorganofunctional alkoxysilanes. The platinum catalyzed addition of allyl glycidyl ether and 1,2-epoxy-4-vinylcyclohexane to alkoxysilanes offers a direct route to the corresponding silyl substituted epoxides.

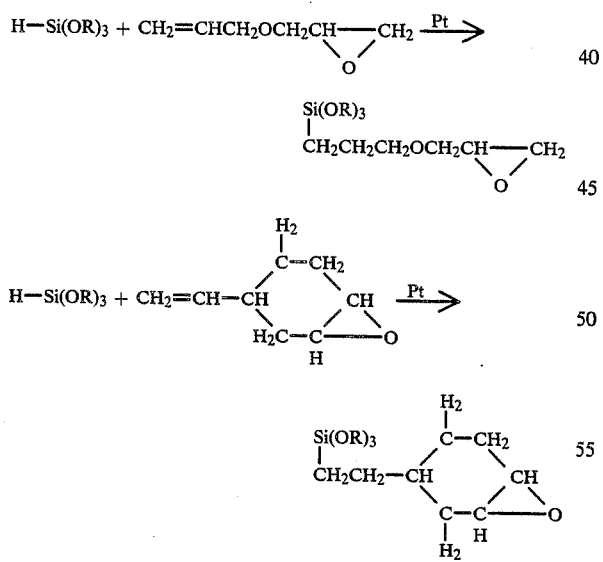

This reaction is well known and has been studied by many investigators, for example: Ger. Offen. No. 1,937,904; Japan No. 75 24,947; and Kremniiorg. Soedin., Tr. Soveshch. 1967, No. 3, 1982.

However, platinum catalyzed hydrosilations are often severely inhibited when nitrogenous impurities are present in either the reacting silane or olefin. In particular, hydrosilations where the olefin is an ethylenically unsaturated epoxide and the silane is an alkoxysilane are especially sensitive to the presence of nitrogenous impurities. For this reaction to be viable, the reactants must be extensively refined to remove nitrogenous impurities prior to the reaction.

OBJECTS OF THE INVENTION

It is therefore an object of this invention to provide a process for producing epoxyorganoalkoxysilanes from ethylenically unsaturated epoxides and alkoxysilanes in the presence of nitrogenous impurities.

Another object of this invention is to provide a process for producing epoxyorganoalkoxysilanes through a catalyzed hydrosilation reaction of ethylenically unsaturated epoxides with alkoxysilanes which eliminates the need for extensive purification of the reactants to remove nitrogenous impurities.

SUMMARY OF THE INVENTION

The process of the invention uses rhodium catalysts to promote the hydrosilation of epoxides with alkoxysilanes in the presence of nitrogenous impurities:

The process of the invention comprises reacting
(a) an ethylenically unsaturated epoxide of the formula:

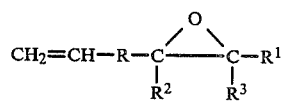

wherein R can be a single bond, alkylene or oxyalkylene, optionally containinq alkyl pendant groups; $R^1$ can be hydrogen, alkyl or oxyalkyl, straight, branched or cyclic; $R^2$ and $R^3$ can individually be hydrogen, alkyl or oxyalkyl, straight, branched or cyclic, or both $R^2$ and $R^3$ can be either alkylene or oxyalkylene and combine together to form a 5 to 12 carbon cyclic ring, optionally containing alkyl pendants; and the number of carbon atoms in R, $R^1$, $R^2$ and $R^3$ are such that the total number of carbons in the epoxide is from 4 to 50;

with (b) an alkoxysilane of the formula:

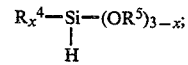

ps wherein $R^4$ and $R^5$ are alkyl groups individually containing from 1 to 10 carbon atoms, and x is 0, 1 or 2;

in the presence of a catalytically effective amount of a rhodium catalyst;

wherein at least one of said epoxide and said alkoxysilane contain nitrogenous impurities; to produce an epoxyorganoalkoxysilane of the formula:

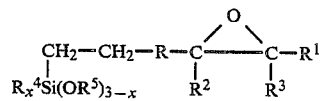

wherein R, $R^1$, $R^2$, $R^3$, $R^4$, $R^5$ and x are as defined above.

DETAILED DESCRIPTION OF THE INVENTION

According to the process of the invention, the hydrosilation of an ethylenically unsaturated epoxide with an alkoxysilane, as described above, is catalyzed by a rhodium catalyst to produce high yields of epoxyorganoalkoxysilanes in the presence of nitrogenous impurities, which are commonly present in the reactants. Nitrogenous impurities suppress the activity of the known platinum catalyst in this reaction.

The inventive process therefore eliminates the need for performing time consuming and costly purification of reactants to remove nitrogenous impurities prior to hydrosilation.

NITROGENOUS IMPURITIES

Nitrogenous impurities commonly occur in either the epoxide or the alkoxysilane, usually as by products of the processes used to prepare the reactants. Usually, the nitrogenous impurities are amines, including primary, secondary and tertiary amines, as well as diamines and silylamines. As used herein, the term nitrogenous impurity refers to any nitrogen containing impurity which impedes the catalytic action of platinum in the hydrosilation of an ethylenically unsaturated epoxide with an alkoxysilane. Generally, the presence of nitrogenous impurities in amounts above about 25 parts per million interferes with platinum catalysis.

EPOXIDES

The ethylenically unsaturated epoxides useful in this invention are those of the formula $$CH_2=CH-R-\underset{R^2}{C}\overset{O}{\overset{}{\diagdown}}\underset{R^3}{C}-R^1$$

wherein R can be a single bond, alkylene or oxyalkylene, optionally containing alkyl pendant groups; $R^1$ can be hydrogen, alkyl or oxyalkyl, straight, branched or cyclic; $R^2$ and $R^3$ can individually be hydrogen, alkyl or oxyalkyl, straight, branched or cyclic; or both $R^2$ and $R^3$ can be either alkylene or oxyalkylene and combine together to form a 5 to 12 carbon cyclic ring, optionally containing alkyl pendants; and the number of carbon atoms in R, $R^1$, $R^2$ and $R^3$ are such that the total number of carbons in the epoxide is from 4 to 50; preferably from 4 to 25.

Particularly preferred epoxides are allyl qlycidyl ether and 1,2-epoxy- 4-vinylcyclohexane.

ALKOXY SILANES

The alkoxy silanes useful in this invention may be represented by the following formula:

$$\underset{H}{\overset{}{R_x^4-Si-(OR^5)_{3-x};}}$$

wherein $R^4$ and $R^5$ are alkyl groups individually containing from one to ten carbon atoms, inclusive, and x is 0, 1 or 2. Preferably, $R^4$ and $R^5$, contain from 1 to 4 carbon atoms.

The trialkoxysilanes are preferred, for which x is 0 in the above formula. Particularly preferred are trimethoxysilane and triethoxysilane.

RHODIUM CATALYST

The rhodium catalyst can be any form of rhodium which acts to catalyze the hydrosilation of the epoxide and the alkoxysilane. Rhodium catalysts useful in the process of the invention include:

Rhodium metal, either alone or on a support such as carbon black or alumina;

Soluble compounds of rhodium, such as rhodium trichloride, rhodium (III) 2,4-pentanedionate, dicarbonylrhodium (I) 2,4-pentanedionate;

Complexes of rhodium with phosphines, such as tris(triphenylphosphine)rhodium (I) chloride, tris(triphenylphosphine)rhodium (I) carbonylhydride, triphenylphosphinecarbonylrhodium (I) 2,4-pentanedionate; and Rhodium containing dimers, such as bis-(chlorodicarbonylrhodium) and 1,5-cyclooctadienerhodium (I) chloride dimer.

The concentration of the rhodium catalyst is generally dependant on the alkoxysilane and ranges from 0.000010 to 0.05 mole percent with respect to the alkoxysilane. It is preferred to use no more of the rhodium catalyst than is necessary to be catalytically effective.

EPOXYORGANOALKOXYSILANES

The epoxyorganofunctional alkoxysilanes produced according to the invention can be represented by the formula:

$$CH_2-CH_2-R-\underset{R^2}{C}\overset{O}{\overset{}{\diagdown}}\underset{R^3}{C}-R^1$$
$$R_x^4-Si-(OR^5)_{3-x}$$

wherein R, $R^1$, $R^2$, $R^3$, $R^4$, $R^5$ and x are as defined above.

Preferred products are (3-glycidoxypropyl) trimethoxysilane and beta-(3,4-epoxycyclohexyl) ethyltrimethoxysilane.

CONDITIONS

This reaction can be carried out over a wide range of temperatures and pressures. The usual temperature range is from about 50° C. to 175° C. The preferred temperature range is from about 75° C. to 125° C. Usually the reaction will be conducted at atmospheric pressure.

The duration of the reaction will vary depending on the amount of rhodium catalyst and the reaction temperature. Higher catalyst concentrations and reaction temperatures will result in a shorter reaction time. Usually, a reaction time of one hour is sufficient.

The use of a solvent is not generally necessary in the process of the invention. If a solvent is employed, generally any hydrocarbon may be used as the solvent. Examples of useful solvents include octane, xylene and triisopropylbenzene.

Whereas the exact scope of the instant invention is set forth in the appended claims, the following specific examples illustrate certain aspects of the present invention, and more particularly, point out methods of evaluating the same. However, the examples are set forth for illustration only and are not to be construed as limitations on the present invention except as set forth in the appended claims. All parts and percentages are by weight unless otherwise specified.

EXAMPLES

The following examples 1 through 12 demonstrate that in the process of the invention a rhodium catalyst effectively promotes the hydrosilation reaction of unsaturated epoxides with alkoxysilanes in the presence of nitrogenous impurities. Yields of from 60% to 80% of the desired products are produced. Unless otherwise indicated yields were determined by gas chromatography.

The comparative examples below show that although both rhodium (Comparative Example A) and platinum (Comparative Example B) catalysts produce good yields in the absence of nitrogenous impurities, the activity of platinum catalysts is drastically suppressed by the presence of nitrogenous impurities. Indeed, less than 5% yield of product is produced in Comparative Exaxples C, D and E and Comparative Example F produced no detectable amount of the desired product.

EXAMPLE 1

A 50 ml 3 neck flask was equipped with a stirring bar, thermometer, 20 ml addition funnel and reflux condenser topped with a nitrogen inlet tube. The flask was charged with 9.4 g (0.82mol) allyl glycidyl ether and 50 ppm tris(triphenylphosphine)rhodium (I) chloride (4.3 mg). The reaction mixture was heated to 110° C. at which time 10.0 g (0.82 mol) trimethoxysilane, containing approximately 1% nitrogenous impurities, primarily dimethylamine, bis(dimethylamino)methane and dimethylaminodimethoxysilane was added dropwise over a period of 15–30 minutes. The reaction was exothermic. After the addition was complete the reaction mixture was cooled to room temperature and gas chromatographic (GC) analyses showed that the desired product (3-glycidoxypropyl)trimethoxysilane, was formed in greater than 65% yield.

EXAMPLE 2

The reaction was run as described in Example 1 except that 50 ppm 5% rhodium on carbon support was used as the catalyst. The desired product (3-glycidoxypropyl)trimethoxysilane was formed in greater than 75% yield.

EXAMPLE 3

The reaction was run as described in Example 1 except that 50 ppm dicarbonylrhodium (I) 2,4-pentanedionate was used as the catalyst. The desired product (3-glycidoxypropyl)trimethoxysilane, was formed in greater that 70% yield.

EXAMPLE 4

A 50 ml 3-neck flask was equipped with a stirring bar, thermometer, 20 ml addition funnel and reflux condenser topped with a nitrogen inlet tube. The flask was charged with 11.3 g (0.1 mol) allyl glycidyl ether and 50 ppm 5% rhodium on carbon support. The reaction mixture was heated to 80° C. and the addition of 12.2 g (0.1 mol) trimethoxysilane, which contained 1% nitrogenous impurities, primarily dimethylamine, bis(dimethylamino)methane and dimethylaminodimethoxysilane, was begun. The temperature of the reaction mixture was maintained between 80° and 100° C. throughout the addition. After the addition was completed the reaction mixture was cooled to room temperature and GC analysis showed that the desired product (3-glycidoxypropyl)trimethoxysilane had been formed in greater than 80% yield.

EXAMPLE 5

The reaction was run as described in Example 4, except that 10 ppm 5% rhodium on carbon support was used as the catalyst. The desired product (3-glycidoxypropyl)trimethoxysilane was formed in greater than 70% yield.

EXAMPLE 6

The reaction was run as described in Example 4, except that 1,2-epoxy-4-vinylcyclohexane was used as the starting unsaturated epoxide. The desired product $\beta$-(3,4-epoxycyclohexyl)ethyltrimethoxysilane was formed in greater than 70% yield.

EXAMPLE 7

The reaction was run as described in Example 4, except that 50 ppm tris(triphenylphosphine) rhodium (I) chloride was used as the catalyst and 1,2-epoxy-4-vinylcyclohexane was used as the starting unsaturated epoxide. The desired product $\beta$-(3,4-epoxycyclohexyl)ethyltrimethoxy silane was formed in greater than 60% yield.

EXAMPLE 8

The reaction was run as described in Example 4, except that 50 ppm bis-(chlorodicarbonylrhodium) was used as the catalyst and 1,2-epoxy-4-vinylcyclohexane was used as the starting unsaturated epoxide. The desired product $\beta$-(3,4-epoxycyclohexyl)ethyltrimethoxy silane was formed in greater than 70% yield.

EXAMPLE 9

The reaction was run as described in Example 4, except that 50 ppm triphenylphosphine carbonylrhodium (I) 2,4-pentanedionate was used as the catalyst and 1,2-epoxy-4-vinylcyclohexane was used as the starting unsaturated epoxide. The desired product $\beta$-(3,4-epoxycyclohexyl)ethyl trimethoxysilane was formed in greater than 70% yield.

EXAMPLE 10

The reaction was run as described in Example 1, except that 50 ppm triphenylphosphine carbonylrhodium (I) 2,4-pentanedionate was used as the catalyst. The desired product (3-glycidoxypropyl)trimethoxysilane was formed in greater than 60% yield.

EXAMPLE 11

The reaction was run as described in Example 1, except that 50 ppm bis-(chlorodicarbonylrhodium) was used as the catalyst. The desired product (3-glycidoxypropyl)trimethoxysilane was formed in greater than 60% yield.

EXAMPLE 12

The reaction was run as described in Example 1, except that the 1,5-cyclooctadiene rhodium (I) chloride dimer was used as the catalyst. The desired product (3-glycidoxypropyl)trimethoxysilane was formed in qreater than 60% yield.

COMPARATIVE EXAMPLE A

A 50 ml 3-neck flask was equipped with a stirring bar, thermometer, 20 ml addition funnel and reflux condenser topped with a nitrogen inlet tube. The flask was charged with 9.4 g (0.082 mol) allyl glycidyl ether and 50 ppm 5% rhodium on carbon support. The reaction mixture was heated to 110° C. at which time 10.0 g (0.082 mol) trimethoxysilane that was free of any nitrogenous containing contaminants was added dropwise over a period of 15–30 minutes. The reaction exothermed during the course of the addition to 150° C. After the addition was complete the reaction mixture was allowed to cool to room temperature. GC analysis showed that greater than 70% of the desired product (3-glycidoxypropyl)trimethoxysilane had been formed.

COMPARATIVE EXAMPLE B

The reaction was run as described in Example A with the exception that 50 ppm $H_2PtCl_6$ (chloroplatinic acid) was used as the catalyst. The desired product (3-glycidoxypropyl)trimethoxysilane was formed in greater than 70% yield.

COMPARATIVE EXAMPLE C

The reaction was run as described in Example B with the exception that the trimethoxysilane used contained approximately 1% of nitrogenous containing materials, which were primarily dimethylamine, bis(dimethylamino)methane and dimethylaminodimethoxysilane. There was an exotherm to 125° C. upon adding the trimethoxysilane; however, a gas chromatograph analysis of the reaction mixture after the addition of trimethoxysilane was complete revealed that the desired product (3-glycidoxypropyl)trimethoxysilane had been formed in less than 5% yield.

COMPARATIVE EXAMPLE D

The reaction was run as described in Example C, however, 50 ppm platinum dichloride ethylenediamine was used as the catalyst. The desired product (3-glycidoxypropyl)trimethoxysilane was formed in less than 5% yield.

COMPARATIVE EXAMPLE E

The reaction was run as described in Example C, however, the catalyst used was 50 ppm 5% platinum on carbon support. The desired product (3-glycidoxypropyl)trimethoxysilane was formed in less than 5% yield.

COMPARATIVE EXAMPLE F

The reaction was run as described in Example C, except that 1,2-epoxy-4-vinylcyclohexane was used as the starting unsaturated epoxide. No products were detected by GC.

We claim:

1. A process for producing epoxyorganoalkoxysilanes from reactants which contain nitrogenous impurities which comprises reacting
   (a) an ethylenically unsaturated epoxide of the formula:

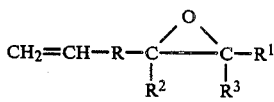

wherein R can be a single bond, alkylene or oxyalkylene, optionally containing alkyl pendant groups; $R^1$ can be hydrogen, alkyl or oxyalkyl, straight, branched or cyclic; $R^2$ and $R^3$ can individually be hydroqen, alkyl or oxyalkyl, straight, branched or cyclic, or both $R^2$ and $R^3$ can be either alkylene or oxyalkylene and combine together to form a 5 to 12 carbon cyclic ring, optionally containing alkyl pendants; and the number f carbon atoms in R, $R^1$, $R^2$ and $R^3$ are such that the total number of carbons in the epoxide is from 4 to 50;
with (b) an alkoxysilane of the formula:

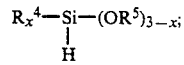

wherein $R^4$ and $R^5$ are alkyl groups individually containing from 1 to 1carbon atoms, and x is 0, 1 or 2;
in the presence of a catalytically effective amount of a rhodium catalyst;
wherein at least one of said epoxide and said alkoxysilane contain nitrogenous impurities; to produce an epoxyorganoalkoxysilane of the formula:

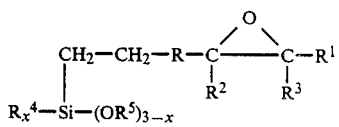

wherein R, $R^1$, $R^2$, $R^3$, $R^4$, $R^5$ and x are as defined.

2. The process of claim 1 wherein $R^4$ and $R^5$ contain from 1 to 4 carbon atoms.

3. The process of claim 2 wherein X equals 0.

4. The process of claim 3 wherein the alkoxysilane is trimethoxysilane or triethoxysilane.

5. The process of claim 1 wherein the number of carbons in the epoxide is from 4 to 25.

6. The process of claim 5 wherein the epoxide is allyl glycidyl ether.

7. The process of claim 5 wherein the epoxide is 1,2-epoxy-4 vinylcyclohexane.

8. The process of claim 1 wherein the amount of nitrogenous impurities is above about 25 parts per million.

9. The process of claim 1 wherein the rhodium catalyst is optionally supported rhodium metal.

10. The process of claim 1 wherein the rhodium catalyst is a soluble compound of rhodium.

11. The process of claim 10 wherein the rhodium catalyst is rhodium trichloride, rhodium (III)-2,4-pentanedionate, or dicarbonylrhodium (I)-2,4-pentanedionate.

12. The process of claim 1 wherein the rhodium catalyst is a complex of rhodium with phosphines.

13. The process of claim 12 wherein the rhodium catalyst is tris(triphenylphosphine) rhodium (I) chloride, tris(triphenylphosphine) rhodium (I) carbonylhydride, or triphenylphosphinecarbonyl rhodium (I) 2,4-pentanedionate.

14. The process of claim 1, wherein the catalyst is bis-(chlorodicarbonylrhodium) or 1,5 cyclooctadienerhodium (I) chloride dimer.

15. The process of claim 2 wherein the epoxide is allyl glycidyl ether or 1,2-epoxy-4-vinylcyclohexane.

16. The process of claim 3 wherein the epoxide is allyl glycidyl ether or 1,2-epoxy-4-vinylcyclohexane.

17. The process of claim 4 wherein the epoxide is allyl glycidyl ether or 1,2-epoxy-4-vinylcyclohexane.

* * * * *